(12) United States Patent
Muir et al.

(10) Patent No.: US 8,247,212 B2
(45) Date of Patent: Aug. 21, 2012

(54) CIRCULATION OF ALGAL BROTH BY THERMALLY-INDUCED CONVECTION

(75) Inventors: Mark P. Muir, Venice, CA (US); Alan D. Eastman, Salt Lake City, UT (US); Randy Balik, Hermosa Beach, CA (US)

(73) Assignee: Greenfire Partners LLC, Venice, CA (US)

( * ) Notice: Subject to any disclaimer, the term of this patent is extended or adjusted under 35 U.S.C. 154(b) by 1023 days.

(21) Appl. No.: 12/222,503

(22) Filed: Aug. 11, 2008

(65) Prior Publication Data

US 2009/0098637 A1    Apr. 16, 2009

Related U.S. Application Data

(60) Provisional application No. 60/955,297, filed on Aug. 10, 2007.

(51) Int. Cl.
*C12N 1/12* (2006.01)
*A01H 13/00* (2006.01)
*A01G 31/00* (2006.01)

(52) U.S. Cl. .......... 435/257.1; 47/1.4; 47/62 R; 47/59 R

(58) Field of Classification Search ................. 435/257.1
See application file for complete search history.

(56) References Cited

U.S. PATENT DOCUMENTS

| 4,217,728 A | 8/1980 | Shimamatsu |
| 4,473,970 A | 10/1984 | Hills |
| 4,910,912 A | 3/1990 | Lowrey |
| 2009/0130704 A1* | 5/2009 | Gyure .......................... 435/41 |

FOREIGN PATENT DOCUMENTS

| JP | 53132170 | 11/1978 |
| JP | 09000095 | 1/1997 |
| WO | 2005102031 | 11/2005 |

OTHER PUBLICATIONS

Notification of Transmittal of the International Search Report and the Written Opinion of the International Searching Authority, or the Declaration issued in corresponding international application No. PCT/US2008/072785, mailed Jan. 19, 2009.

* cited by examiner

*Primary Examiner* — Delia Ramirez
(74) *Attorney, Agent, or Firm* — Cooley LLP

(57) ABSTRACT

The present invention provides a method of circulating algae in growing containers using thermally-induced convection techniques. In particular, a method of growing algae by providing a thermal gradient in algae containing medium is disclosed.

13 Claims, 5 Drawing Sheets

Low = 1
High = 2

Low = 7
High = 8

Low = 15
High = 16

Low = 3
High = 4

Low = 10
High = 12

Low = 17
High = 18

Low = 5
High = 6

Low = 13
High = 14

Low = 19
High = 20

Start　　　　　　　　3 seconds　　　　　　　8 seconds 10 seconds　　　　　　16 seconds

Start        1.5 seconds        3.5 seconds 5.0 seconds        6.5 seconds

CIRCULATION OF ALGAL BROTH BY THERMALLY-INDUCED CONVECTION

CROSS REFERENCE TO RELATED APPLICATIONS

This application claims priority to U.S. Provisional Application No. 60/955,297 filed Aug. 10, 2007, which is herein incorporated by reference in its entirety.

FIELD OF THE INVENTION

This invention is related to methods of circulating algal broth in growing containers to enhance the growth rate of algae. In particular, the methods utilize convection induced by thermal gradients alone or in combination with other mechanical and/or chemical means to circulate the algal broth in algae-growing containers.

BACKGROUND OF THE INVENTION

Algae growth is increasingly desirable because of the demand for clean energy. Algae growth ponds are typically on the order of 4" in depth because photosynthetically available radiation (PAR) does not effectively penetrate to depths greater than that. Nevertheless, usually algae only use about 10% of the PAR in incident sunlight for photosynthesis. There is great need for methods to promote algae growth, e.g., methods that allow greater percentage of the incident sunlight to be utilized for photosynthesis and promote a significantly greater mass of algae for a given surface area per unit time.

SUMMARY OF THE INVENTION

The present invention is based, in part, on the discovery that induction of convection currents by thermal gradients provides circulation of algae-containing growth media in containers. Accordingly, the invention provides methods for circulating growth media in algae-growing containers, e.g., enhances the growth rate of algae as well as the amount of algae that may be produced per unit of surface area.

The present invention provides a method for growing algae comprising providing a thermal gradient in an algae containing medium. The algae containing medium may be in an open container, closed container, semi-closed container, or a closed container which can be opened partially or entirely.

In one embodiment, the algae containing medium is in a container which has a first surface and a second surface, wherein the temperature on the first surface is different from the temperature on the second surface. In some embodiments, the first surface of the container absorbs light differently from the second surface of the container. In other embodiments, the first surface of the container has a color darker than the color of the second surface.

The first surface and the second surface of the container may or may not be in contact with the algae containing medium. In one embodiment, the first surface of the container is in contact with the algae containing medium. In another embodiment, the first surface of the container is not in contact with the algae containing medium. In another embodiment, the first surface of the container has a heating element.

In another embodiment of the invention, the method comprises providing a thermal gradient in an algae containing medium by mixing the algae containing medium with a temperature adjusting entity. The temperature adjusting entity may be a body of fluid, air, or solid entities. The temperature adjusting entity preferably has a temperature different from the algae containing medium. In some embodiments, the temperature adjusting entity is a body of solid entities with a surface temperature different from a surface of the container. In other embodiments, the temperature adjusting entity is a body of solid entities with a surface which absorbs light differently than a surface of the container.

DETAILED DESCRIPTION OF THE INVENTION

Figure 1:
FIG. 1 shows the thermocouple grid pattern of eighteen thermocouples inserted into an algae-growing container to measure temperature differentials inside the container. The numbers to the right of each thermocouple pair represent placements of specific thermocouples where the "high" thermocouple is the one closest to the top of the liquid, and the "low" thermocouple is slightly below the center of the liquid.
Figure 1:
Figure 1:
Figure 1:
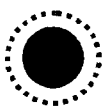
Figure 1:
Figure 1:
Figure 1:
Figure 1:
Figure 1:
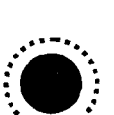

The present invention is based, in part, on the discovery that induction of convection currents by thermal gradients provides circulation of algae-containing growth media in containers. Accordingly, the invention provides methods for circulating growth media in algae-growing containers, e.g., enhances the growth rate of algae as well as the amount of algae that may be produced per unit of surface area. The techniques disclosed herein provide ways, e.g., non-mechanical ways to circulate the algae within the growth medium in an algae-growing container, e.g., allows for enhanced algal growth and an increase in the total production of algae for a given surface area per unit time. Thus, the present invention provides a method for growing algae.

In one embodiment, the method comprises providing a thermal gradient in an algae containing medium. The algae containing medium may be in an open container, closed container, or semi-closed container. Alternatively, the algae containing medium is in a closed container, which can be opened partially or entirely. Some non-limiting examples of suitable containers for use in the methods of the invention include ponds, plexiglass or glass cylinders, rigid or flexible plastic vessels, tubes, flasks, bags, or any container capable of containing algal growth medium and sustaining algal growth. Other appropriate bioreactors or containers suitable for use will be apparent to those of skill in the art.

In general, algae refers to one or more groups of relatively simple living aquatic organisms that capture light energy through photosynthesis, using it to convert inorganic substances into organic matter. Algae are photosynthetic organisms that occur in most habitats. Algae vary from small and single-celled to complex multicellular species, such as the giant kelps that grow to 65 meters in length.

Algae can be in eukaryotic or prokaryotic forms, e.g., plants, protists, blue-green algae, etc. Algae range from single-cell organisms to multicellular organisms, some with fairly complex differentiated forms and (if marine) called seaweeds. All lack leaves, roots, flowers, seeds and other organ structures that characterize higher plants (vascular plants).

In one embodiment of the invention, circulation of the algae-containing medium is induced by creating a thermal gradient by passive means. By "passive means" it is meant that only energy from incident sunlight will be utilized to induce circulation. In some embodiments, formation of thermal gradients by passive means may entail providing at least two surfaces that are in contact with the algae-containing medium, wherein the at least two surfaces have different temperatures. In one such embodiment, the algae containing medium is in a container which has a first surface and a second surface, wherein the temperature on the first surface is different from the temperature on the second surface. Both the first surface and second surface may be in contact with the algae containing medium.

In other embodiments, the first surface and the second surface are not in contact with the algae containing medium. For example, a container holding the algae-containing medium may be placed on a first surface and a second surface, wherein the first surface has a different temperature than the second surface. In another embodiment, the first surface is in contact with the algae containing medium. In yet another embodiment, the first surface is not in contact with the algae containing medium.

In another embodiment of the invention, the algae containing medium is in a container which has a first surface and a second surface, wherein the first surface of the container absorbs light differently from the second surface of the container. The first surface of the container may have a color darker than the color of the second surface. One non-limiting example illustrating this passive technique of inducing circulation by thermal gradients is to divide a growth pond into segments along a longitudinal axis. Paint or otherwise darken/blacken alternate segments of the bottom surface of the pond before filling the pond with algae containing medium (i.e. algal broth). Once the pond has been filled and is exposed to incident light, the medium above the darkened segments will absorb heat from sunlight, thus inducing convection between the parts of the container over the dark and light segments. Alternatively, the internal or external surface of a container or vessel (e.g., glass containers, rigid or flexible plastic vessels or tubes) holding the algae containing medium may be darkened by using paint or other means to produce dark and light areas which will induce convection upon application of heat from sunlight or other external light source. Any approach for producing alternating dark and light surfaces either on the container holding the algal broth itself or beneath such a container are suitable for use in the methods of the invention.

In some embodiments, containers or ponds covered with a translucent material (e.g., glass or plastic) that have an air space between the algae containing medium and the translucent material may have one-way valves installed in the translucent material so that air and other gases in the air space that have been heated can escape to the atmosphere. This allows the surface of the algae containing medium to cool, thus maintaining the temperature gradient and the convective circulation.

Circulation of algae containing medium within containers may also be achieved by creating thermal gradients by active means. By "active means" it is meant that mechanical or chemical processes will be used to induce circulation. Inducing circulation by such means might be particularly important in the periods after sunrise and before sunset when the amount of incident sunlight is relatively small and unlikely to be sufficient to either induce or sustain circulation by passive means. Mechanical means may include, but are not limited to, paddle wheels, which are often used for so-called 'raceway ponds', external rollers used in combination with tubular flexible growth containers, and sparged gases.

In some embodiments, active techniques to induce or maintain circulation via convection cell can include forced heating of portions of the algae containing medium or different surfaces of a container holding the algae containing medium. In one embodiment, the algae containing medium has a first body of medium and a second body of medium, wherein the first body of medium has a temperature different from the temperature of the second body of medium. In another embodiment, a first surface of a container holding algae containing medium has a heating element. Heating elements can be placed in the bottoms of growth containers with each element being located at a spacing equal to the desired spacing of convection cells within the container. In an alternative embodiment, heated water or other fluid can be pumped through pipes at the bottom of the containers. These pipes can be covered with thermal insulation except at locations corresponding to desired centers of convection. The heated water may be, for example, geothermal fluids or cooling water from power plants or other industrial facilities. Water may also be heated by passing it through pipes embedded in heat-absorbing materials (e.g., black-painted concrete pads). In one embodiment, waste heat from the production of biodiesel is recycled to the algae growth containers by inclusion of those containers in the cool side of the transesterification plant heat exchangers.

In another embodiment of the invention, a thermal gradient in the algae containing medium may be produced by mixing the medium with a temperature adjusting entity. A temperature adjusting entity may be a body of fluid, air, or solid entities and preferably has a temperature different from the algae containing medium. The temperature of the temperature adjusting entity may be higher or lower than the temperature of the algae containing medium. Some non-limiting examples of temperature adjusting entities include, superheated water, steam, heated stones or rocks, or cooled water, such as that produced as a byproduct of industrial processes. In another embodiment, the temperature adjusting entity is a body of solid entities with a surface temperature different from a surface of the container. In yet another embodiment, the temperature adjusting entity is a body of solid entities with a surface which absorbs light different from a surface of the container.

Circulation may also be induced by creating thermal gradients using a combination of active and passive means. For example, a relatively minor thermal gradient is required to induce circulation if gas is sparged in the growth medium. It is common to sparge carbon dioxide in algae ponds and photobioreactors. Thus, combining sparging of carbon dioxide with the creation and maintenance of a relatively minor thermal gradient induces circulation in a relatively cost effective manner. A combination of other types of mechanical means, such as paddle wheels or external rollers, with one of the passive means for creating thermal gradients described herein is also contemplated.

The examples which follow are set forth to illustrate the present invention, and are not to be construed as limiting thereof.

EXAMPLES

Example 1

Construction of Experimental Apparatus

To measure convection currents induced by thermal or mechanical means, a suitable container in which algae could be grown was constructed. A PVC frame, approximately 18×24×5 inches, was built and inserted into an 8-mil thick HDPE bag (TRM Manufacturing, Corona, Calif.), of nominal size 24×48 inches. A grid of eighteen Type K thermocouples, spaced as shown in FIG. 1, was inserted into the bag to measure temperature differentials inside the bag under different conditions. The spots where the thermocouples pierced the bag were sealed with silicone sealant. A 24-inch aquarium bubbler was also inserted into the bag at the bottom, close to one side, and a vent tube was inserted into the top of the bag. As with the thermocouples, all piercings of the bag were sealed with silicone sealant. An Altman stage lamp with a calibrated controller was hung above the bag to reproducibly simulate sunlight.

Figure 2:
FIG. 2 depicts the set-up of the experimental apparatus for a baseline experiment, in which a black background is placed underneath the apparatus. The lamp provides simulated sunlight.
Figure 3:
FIG. 3 illustrates the set-up of the experimental apparatus for a convection experiment, in which a white background is positioned to partially cover the bottom surface of the apparatus.

For baseline experiments, a black background was placed under the entire area of the bag (see FIG. 2). For the convection experiments, a piece of white cardboard was placed under approximately ¾ of the area of the bag. FIG. 3 shows the setup of the experimental apparatus before the addition of water for a convection experiment (e.g. with the white background).

Prior to the start of experiments, the bag was filled with water at room temperature. Green food coloring was added to the bag to simulate the presence of algae. In addition, roughly 250 g of orange air-rifle pellets, which have a density similar to that of water, were added to visualize the movement of currents in the bag under different experimental conditions.

Example 2

Thermally-induced Convection

To determine whether the presence of two different colored backgrounds underneath a putative algae-growing container was sufficient to produce significant thermal convection currents, the lamp positioned over the experimental apparatus described in Example 1 was turned on and resulting currents, visualized by the movement of the air-rifle pellets, were recorded by a video camera.

Figure 4:
FIG. 4 shows a series of still photographs obtained from a video recording of the motion of orange-colored pellets within a fluid-filled container upon exposure to illumination. The container was placed on a differentially colored background: ¼ of the background was black, while the remaining ¾ was white.
Figure 4:
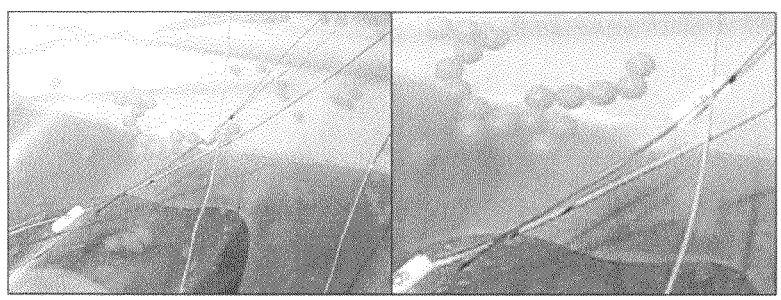

The lamp was adjusted to deliver one mole of photons per minute, which is roughly equivalent to a moderately sunny day. The temperature was taken at each thermocouple every 20 seconds, and recorded by a data logger. In the baseline experiment (black background placed underneath the experimental apparatus), the temperature in the bag rose relatively monotonically, and little motion of the pellets was observed. In the convection experiment (white background placed under approximately ¾ of the experimental apparatus), within 15 minutes of the start of illumination, some of the pellets rose to the surface of the water. After about 45 minutes, the pellets were rising to the surface, and were circulating in the bag. The observed motion of the pellets can be seen in the stills taken from the video recording (FIG. 4).

The results of this experiment demonstrate that in the absence of differential backgrounds, no thermal motion is detected. However, in the presence of different colored backgrounds beneath the bag (e.g. putative algae-growing container), thermal convection induced by light energy roughly equivalent to sunlight is established soon after the light source is present and continues to grow with time. These findings suggest that significant thermal convection can be established in algae-growing containers with typical sunlight, and that the established thermal convection can be used to circulate fluid (e.g. growth media) inside the container.

Example 3

Sparging-induced Convection

To compare the currents induced by thermal convection to those induced by a mechanical means, air was introduced into the bag through the aquarium bubbler and the resulting motion of the pellets was recorded.

Figure 5:
FIG. 5 shows a series of still photographs obtained from a video recording of the motion of orange-colored pellets within a fluid-filled container upon the bubbling of air through the container.
Figure 5:
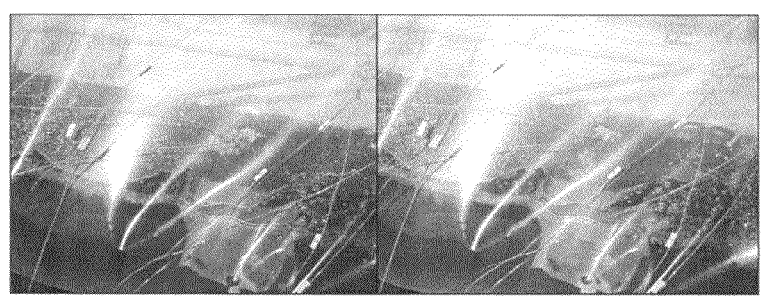

For these experiments, the apparatus was positioned such that the bubbler was located on the side of the apparatus located above the black background so that the similarity of convection introduced by thermal gradients or by sparging could be gauged (see FIG. 3 and Example 1). Air was bubbled into the bag with the sparger (i.e., the aquarium bubbler.) Although the flow rate of the air was not precisely measured, the air flow through the sparger was considerable. The backgrounds placed underneath the bag (e.g. dark background under ¼ of the bag and a white background under ¾ of the bag) and lamp placement were the same as those described for the experiment in Example 2. Circulation of the orange-colored pellets with the sparged air was faster than with thermal differentials alone, but was essentially identical in pattern. Typical stills from a video recording taken during sparging in the presence of differentially colored backgrounds are shown in FIG. 5. These results show that thermal convection is similar to convection induced by sparging a gas through the liquid, and that such mechanical means of producing convection can be combined with thermally-induced convection to enhance circulation of fluid inside a container, such as an algae growing container.

It is understood that the disclosed invention is not limited to the particular methodology, protocols and materials described as these may vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:
1. A method of inducing circulation in an algae growing medium comprising:
 providing an algae-containing medium in a container, wherein the container has a bottom surface comprising a first segment and a second segment, said first segment absorbing light differently from said second segment; and
 exposing the container to a light source, wherein a continuous thermal gradient is established in the medium following exposure to the light source, thereby producing circulation of the algae in the medium.
2. The method of claim 1, wherein the container is an open container, closed container, or semi-closed container.

3. The method of claim 1, Wherein the container is a closed container which can be opened partially or entirely.

4. The method of claim 1, wherein the temperature on the first segment is different from the temperature on the second segment.

5. The method of claim 1, wherein the bottom surface is in contact with the algae-containing medium.

6. The method of claim 1, wherein the bottom surface is not in contact with the algae-containing medium.

7. The method of claim 1, wherein the first segment of the bottom surface has a color darker than the color of the second segment.

8. The method of claim 1, wherein the container is a pond.

9. The method of claim 1, wherein the container is a glass or plastic vessel.

10. The method of claim 1, wherein the light source is sunlight.

11. The method of claim 1, wherein the container comprises a cover of translucent material, said cover comprising a one-way valve that allows gases to exit the container.

12. The method of claim 1, further comprising sparging a gas into the medium.

13. The method of claim 12, wherein the gas is air or carbon dioxide.

* * * * *